(12) United States Patent
Adoni et al.

(10) Patent No.: US 10,095,979 B2
(45) Date of Patent: Oct. 9, 2018

(54) MODELING FOR FLAVOR PROFILES

(71) Applicant: International Business Machines Corporation, Armonk, NY (US)

(72) Inventors: Siddique M. Adoni, Bangalore (IN); Aveek N. Chatterjee, Bangalore (IN); Dhandapani Shanmugam, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 184 days.

(21) Appl. No.: 14/791,515

(22) Filed: Jul. 6, 2015

(65) Prior Publication Data

US 2017/0011164 A1    Jan. 12, 2017

(51) Int. Cl.
| | |
|---|---|
| G01N 31/00 | (2006.01) |
| G06N 5/04 | (2006.01) |
| G06F 19/00 | (2018.01) |
| G16H 50/50 | (2018.01) |
| G06F 17/50 | (2006.01) |

(52) U.S. Cl.
CPC ........... *G06N 5/04* (2013.01); *G06F 19/3475* (2013.01); *G16H 50/50* (2018.01); *G06F 17/5009* (2013.01)

(58) Field of Classification Search
None
See application file for complete search history.

(56) References Cited

U.S. PATENT DOCUMENTS

| | | | |
|---|---|---|---|
| 4,570,636 A | 2/1986 | Kurose | |
| 6,053,738 A | 4/2000 | Ivey, Jr. | |
| 7,587,331 B2 | 9/2009 | Pelletier | |
| 8,004,152 B2 | 8/2011 | Fung et al. | |
| 9,314,631 B2* | 4/2016 | Avitall | A61N 1/36139 |
| 2008/0234604 A1 | 9/2008 | Burgmans | |
| 2009/0234196 A1 | 9/2009 | Suzuki et al. | |
| 2014/0143020 A1* | 5/2014 | Wolfe | G06T 11/206 |
| | | | 705/7.33 |
| 2014/0172041 A1* | 6/2014 | Draghici | A61N 1/0548 |
| | | | 607/45 |
| 2015/0217115 A1* | 8/2015 | Avitall | A61N 1/36139 |
| | | | 607/58 |
| 2015/0276700 A1* | 10/2015 | Goel | G01N 33/02 |
| | | | 73/865.7 |

OTHER PUBLICATIONS

Ranasinghe et al. "Simulating the sensation of taste for immersive experiences." Proceedings of the 2013 ACM international workshop on Immersive media experiences. ACM, 2013, pp. 29-34.*
Ranasinghe, Nimesha, et al. "Digital taste and smell communication." Proceedings of the 6th international conference on body area networks. ICST (Institute for Computer Sciences, Social-Informatics and Telecommunications Engineering), 2011.*
U.S. Appl. No. 15/165,250, filed May 26, 2016, Entitled "Modeling for Flavor Profiles".
List of IBM Patents or Patent Applications Treated as Related, Dated May 26, 2016, 2 pages.
Ajdukovic, Dean, "The Relationship between Electrode Area and Sensory Qualities in Electrical Human Tongue Stimulation", printed on Mar. 30, 2015, pp. 1-2, <http://informahealthcare.com/doi/abs/10.3109/00016488409107548>.
Bognar, Katalin, "Modelling the taste of food—tasting by computer", Institute of Mathematics and Informatics at University of Kossuth Lajos, Debrecen, Hungary, Printed on Mar. 30, 2015, pp. 1-6, <http://www.inf.unideb.hu/~bognar/Pages/modell.htm>.
Cruz et al., "Thermal stimulation of taste", Letters to Nature, printed on Mar. 30, 2015, 1 page, <http://www.nature.com/nature/journal/v403/n6772/abs/403889a0.html>.
Marks, Paul, "Electrode recreates all four tastes on your tongue", Nov. 20, 2013, NewScientist, Magazine issue 2944, pp. 1-7, <http://www.newscientist.com/article/mg22029444.500-electrode-recreates-all-four-tastes-on-your-tongue.html#.VRqed2NueOZ>.
Nakamura et al., "Augmented Gustation using Electricity", Conference AH'11, Mar. 12-14, Tokyo, Japan Copyright © 2011 ACM 978-1-4503-0426-9/11/03, pp. 1-2, <http://dl.acm.org/citation.cfm?id=1959860&dl=ACM&coll=DL&CFID=429255087&CFTOKEN=67272912>.
Ranasinghe, Nimesha, "Digital Taste Interface", Printed on Mar. 30, 2015, Copyright © 2013, pp. 1-4, <http://nimesha.info/digitaltaste.html#dti>.
Toko, Kiyoshi, "Kansei Biosensor and IT Society", printed on Mar. 30, 2015, IEEJ Transactions on Sensors and Micromachines, vol. 124, Issue 7, 2004, pp. 1-2, <http://adsabs.harvard.edu/abs/2004IJTSM.124..229T>.
Varshney et al., "Cognition as a Part of Computational Creativity", Proc. 12th IEEE Int. Conf. on Cognitive Informatics & Cognitive Computing (ICCI*CC'13), © 2013 IEEE, pp. 36-43.

(Continued)

*Primary Examiner* — Anna Skibinsky
(74) *Attorney, Agent, or Firm* — Stephanie L. Carusillo

(57) ABSTRACT

A method, computer program product, and system for generating flavor profile models are provided. An alpha flavor model is determined. An electrode signal is transmitted to a taste simulator based on the alpha flavor model. User feedback is received. A variance between the alpha flavor model and the user feedback is determined. The variance is compared to a predetermined threshold. In response to determining that the variance is greater than the predetermined threshold, a beta flavor model is generated.

13 Claims, 3 Drawing Sheets

(56) References Cited

OTHER PUBLICATIONS

"Taste and Flavour for Researchers", Institute of Food Research, Norwich Research Park, Colney, Norwich NR4 7UA, UK, printed on Mar. 30, 2015, pp. 1-3, <http://www.ifr.ac.uk/science-society/resources/#tasteandflavour>.

"Taste and Flavour for Teachers", Institute of Food Research, Norwich Research Park, Colney, Norwich NR4 7UA, UK, printed on Mar. 30, 2015, pp. 1-28, <http://www.ifr.ac.uk/science-society/resources/#tasteandflavour>.

\* cited by examiner

MODELING FOR FLAVOR PROFILES

BACKGROUND OF THE INVENTION

The present invention relates generally to the field of taste profiling, and more particularly to generating flavor profile models.

Taste is a sensory impression of food, or other substance, on the tongue. The sensory impression is produced when a substance in the mouth reacts chemically with taste receptor cells on taste buds. Taste, along with smell and nerve stimulation (e.g., texture, pain, and temperature) determines the flavor of a substance.

In general taste of any food item is characterized by five basic tastes: sweet, sour, salty, bitter, and umami. Each taste is a result of variances in the chemical structure, smell, and nerve stimulation. Virtual taste, i.e., the ability to provide flavor without eating a substance, is an emerging technology. The five taste characteristics can be mimicked via an electronic device, by varying electronic pulses sent to the device when placed on a user's tongue.

SUMMARY

According to one embodiment of the present disclosure, a method for generating flavor profile models is provided. The method includes determining, by one or more processors, an alpha flavor model; transmitting, by one or more processors, an electrode signal to a taste simulator, based on the alpha flavor model; receiving, by one or more processors, a user feedback; determining, by one or more processors, a variance between the alpha flavor model and the user feedback; comparing, by one or more processors, the variance to a predetermined threshold; and in response to a determination that the variance is greater than the predetermined threshold, generating, by one or more processors, a beta flavor model.

According to another embodiment of the present disclosure, a computer program product for generating flavor profile models is provided. The computer program product comprises a computer readable storage medium and program instructions stored on the computer readable storage medium. The program instructions include program instructions to determine an alpha flavor model; program instructions to transmit an electrode signal to a taste simulator, based on the alpha flavor model; program instructions to receive a user feedback; program instructions to determine a variance between the alpha flavor model and the user feedback; program instructions to compare the variance to a predetermined threshold; and in response to a determination that the variance is greater than the predetermined threshold, program instructions to generate a beta flavor model.

According to another embodiment of the present disclosure, a computer system for generating flavor profile models is provided. The computer system includes one or more computer processors, one or more computer readable storage media, and program instructions stored on the computer readable storage media for execution by at least one of the one or more processors. The program instructions include program instructions to determine an alpha flavor model; program instructions to transmit an electrode signal to a taste simulator, based on the alpha flavor model; program instructions to receive a user feedback; program instructions to determine a variance between the alpha flavor model and the user feedback; program instructions to compare the variance to a predetermined threshold; and in response to a determination that the variance is greater than the predetermined threshold, program instructions to generate a beta flavor model.

DETAILED DESCRIPTION

An embodiment of the present invention recognizes the virtual world has yet to provide a means to replicate taste sensory information (i.e., virtual taste). Technological advances have been made to replicate the five basic tastes: salty, sweet, bitter, sour, and umami. However, complete virtual flavor profiles are not available. Often, users would like to taste a dish before they decide to eat at a restaurant. In return, some restaurants would like feedback for a dish before or after the dish is offered. Food manufacturers could use virtual taste to run promotions or receive user feedback on new products. Further, when paired with health information, diet food companies could use virtual taste to create a balance between taste and health of new products.

An embodiment of the present invention provides operations to build taste models for food to be used for virtual tasting. The taste models are used by simulators to deliver electrical pulses to a user's tongue, which mimic the flavor of meals. An embodiment of the present invention provides opportunities for businesses and consumers to taste dishes before purchasing through virtual taste. Further, an embodiment of the present invention provides opportunities for businesses to customize food, to better meet the needs of the customer. Still further, embodiments of the present invention provides a means to suggest and review food for social media.

Figure 1:
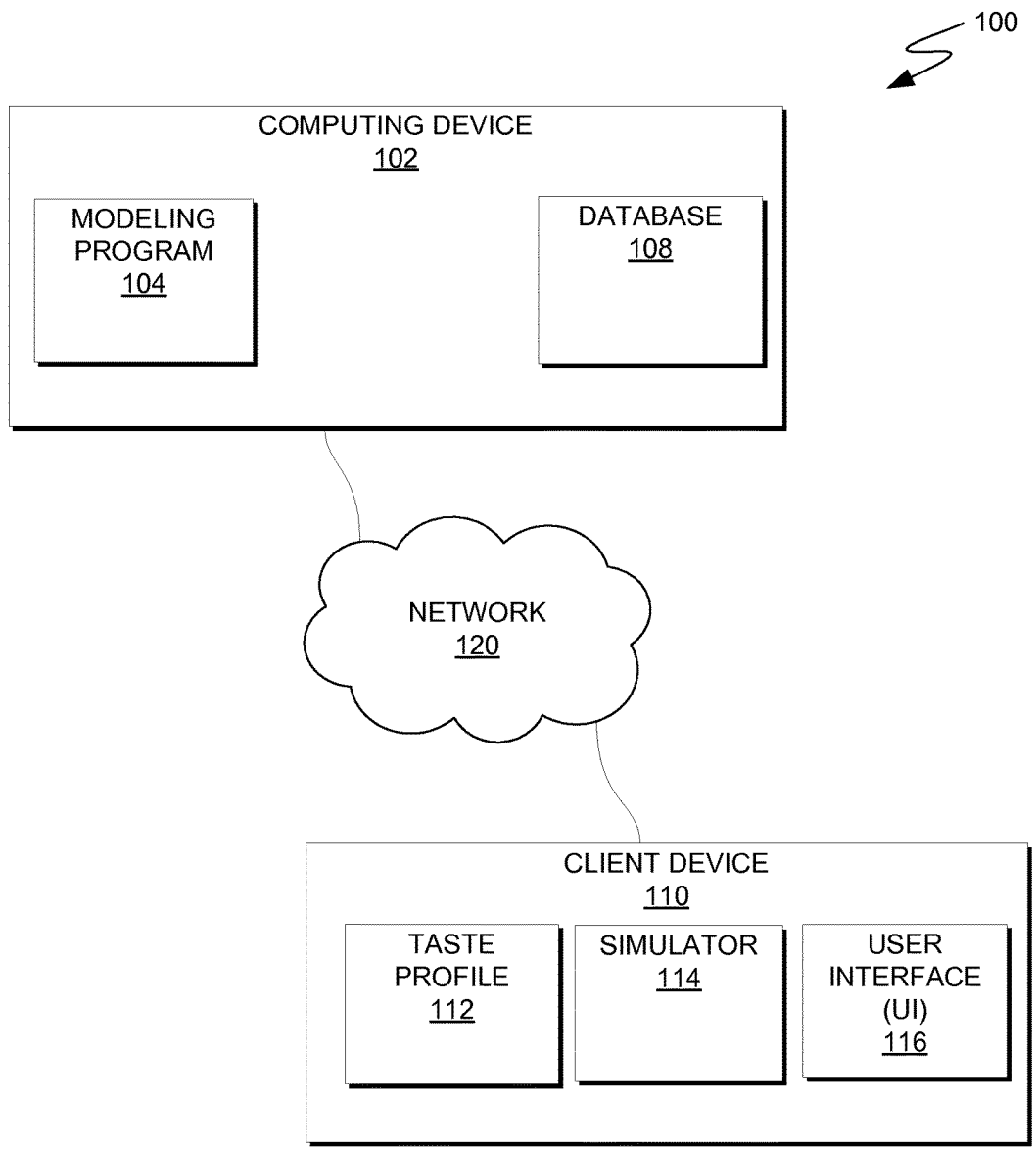
FIG. 1 is a functional block diagram illustrating a computing environment, in accordance with an embodiment of the present disclosure.

The present disclosure will now be described in detail with reference to the Figures. FIG. 1 is a functional block diagram illustrating a computing environment, in accordance with an embodiment of the present disclosure. For example, FIG. 1 is a functional block diagram illustrating computing environment 100. Computing environment 100 includes computing device 102 and client device 110 connected over network 120. Computing device 102 includes modeling program 104 and database 108.

In various embodiments, computing device 102 is a computing device that can be a standalone device, a server, a laptop computer, a tablet computer, a netbook computer, a personal computer (PC), or a desktop computer. In another embodiment, computing device 102 represents a computing system utilizing clustered computers and components to act as a single pool of seamless resources. In general, computing device 102 can be any computing device or a combination of devices with access to client device 110 and with access to and/or capable of executing some or all of modeling program 104 and database 108. Computing device 102 may include internal and external hardware components, as depicted and described in further detail with respect to FIG. 3.

In this exemplary embodiment, modeling program 104 and database 108 are stored on computing device 102. In other embodiments, one or both of modeling program 104 and database 108 may reside on another computing device, provided that each can access and is accessible by each other of modeling program 104, database 108 and client device 110. In yet other embodiments, one or both of modeling program 104 and database 108 may be stored externally and accessed through a communication network, such as network 120. Network 120 can be, for example, a local area network (LAN), a wide area network (WAN) such as the Internet, or a combination of the two, and may include wired, wireless, fiber optic or any other connection known in the art. In general, network 120 can be any combination of connections and protocols that will support communications between computing device 102 and client device 110, in accordance with a desired embodiment of the present invention.

Modeling program 104 operates to determine flavor profile models based on user feedback, laboratory analysis, and crowd sourcing. Modeling program 104 creates taste vectors and health vectors. Additionally, modeling program 104 creates weights used to develop a flavor profile model for a user. The primary function used by modeling program is:

$$\text{Objective Function} = f(\vec{T}, \vec{H}, \vec{w}). \tag{1}$$

Taste vectors include sweet, salty, sour, bitter, and umami (e.g., $T_1$, $T_2$, $T_3$, $T_4$ and $T_5$ respectively). Health vectors include calories, sugar content, cholesterol, metabolic rate, fat, etc. (e.g., $H_1$, $H_2$, ... $H_N$). A weight vector exists for each of the health and taste vectors. In some embodiments, the weight vectors are used by modeling program 104 to modify the impact a vector has on the model. For example, where a user has diabetes, a greater weight is given to the sugar content health vector than the fat content health vector.

In some embodiments, modeling program 104 is used to optimize the objective function for the user. For example, modeling program 104 is used to maximize the health benefits of a dish, while maintaining a desirable taste. In some embodiments, a penalty value is calculated for a dish model when the dish has a poor health value. In other embodiments, a reward value is calculated for a dish model when the dish has a high health value. In still other embodiments, modeling program 104 requires that a threshold health value be met for a dish. Data for health vectors is obtained from laboratory results, including chemical analysis. In some embodiments, some values for taste vectors are obtained from laboratory analysis (e.g., baseline values). In some embodiments, crowd sourcing (e.g., data from multiple program users) is used to determine taste vectors (e.g., baseline data). In some embodiments, modeling program 104 suggests an allowable portion size to satisfy a user's desired health values.

In some embodiments, health vectors are based on recommendations from a user's doctor. For example, a user specifies what ingredients are preferred or to be avoided based on dietary needs. In other embodiments, health vectors are based on regional or religious preferences. For example, ingredients are suggested based on produce available from local farmers.

Database 108 is a data repository that may be written to and read by one or both of modeling program 104 and taste profile 112. User preferences, food analysis, and models may be stored to database 108. In some embodiments, database 108 may be written to and read by programs and entities outside of computing environment 100 in order to populate the repository with baseline flavor and health information. In some embodiments, data from each modeling program 104 user is stored in database 108. In some embodiments, user data in database 108 is used to create baseline data for the taste vectors (e.g., an alpha model). In other embodiments, the user data in database 108 is used to provide recommendations to a user. For example, the user data is used to recommend a restaurant with high ratings from user's with a similar flavor profile model.

In various embodiments of the present disclosure, client device 110 can each respectively be a laptop computer, a tablet computer, a netbook computer, a personal computer (PC), a desktop computer, a personal digital assistant (PDA), a smart phone, or any programmable electronic device capable of communicating with computing device 102 via network 120. Client device 110 includes taste profile 112, simulator 114, and user interface (UI) 116, which execute locally on client device 110.

Taste profile 112 operates to prompt and store user input about food dishes. A taste profile consists of taste vectors, health vectors, and weights. The taste profile is created using simulator 114 and user interface 116. In some embodiments, a user of client device 110 receives electronic pulses via simulator 114 that mimics the flavor profile of a dish. The user interacts with user interface 116 to provide feedback on the flavor profile.

In some embodiments, taste profile 112 allows a user to review food created by a restaurant or food manufacturer. A user provides reviews via interactions with UI 116 on client device 110. In some embodiments, user reviews are quantitative. For example, the review is on a scale of one to five. In some embodiments, user reviews are qualitative. For example, the user provides information that the dish was too salty or not sweet enough.

In some embodiments, taste profile 112 is used to provide recommendations based on a user's likes. For example, a user receives a recommendation to try a new restaurant based on taste profile 112 and reviews from other users. In some embodiments, the results and analysis of the recommendation is based on cuisine, calories, location, price, chefs, etc. For example, the user profile coordinates with a GPS signal to notify the user that a dish matching flavor profile 112 is nearby. In other embodiments, taste profile 112 is used by a chef to modify a dish to a user's taste preferences. For example, before a user visits a restaurant, the user uses simulator 114 and taste profile 112 to fine tune the taste of a dish. In this example, the user saves the taste preferences such that the chef at the restaurant can recreate the taste when the user arrives. In some embodiments, taste profile 112 is used to provide the user with novel dish ideas. For example, taste profile 112 is used to fine tune a recipe to meet the user's likes.

Simulator 114 operates to provide electrode signals to a user's tongue to simulate a taste. Simulator 114 receives electrode signals based on models created by modeling program 104. Simulator 114 is placed on a user's tongue where the electrodes deliver electronic pulses to the user. The electronic pulses are interpreted by the user as flavors. In some embodiments, the electronic pulse replicates a taste characteristic. For example, the user tastes sweet or sour. In other embodiments, the electronic pulse replicates the flavors of a meal. In some embodiments, simulator 114 includes a chemical library, such that a number of chemicals are released to replicate the scent of a dish. In some embodiments, these chemicals are released in the user's mouth such that olfactory stimulation is provided. In some embodiments, the chemical library enhances a user's ability to taste the virtual dish by providing both electronic pulses that are interpreted by the user as flavors as well as olfactory stimulation, via the release of one or more chemicals included in the chemical library. For example, in one embodiment, a user loads a grilled vegetable scent, e.g., in the form of a capsule, into simulator 114. When activated, simulator 114 releases the scent from the capsule while providing the user with electronic pulses that are interpreted by the user as flavors. As a result, the user is provided with a simulation of the taste of a sweet and sour vegetable dish that is served at a restaurant.

Simulator 114 is hardware, which can have several form factors. In one embodiment, simulator 114 is a device made of medical-grade plastic. The device components include a power management integrated circuit (PMIC), actuators, a micro-controller, wireless transceiver, a battery, micro-electrodes, and read-only memory (ROM). In some embodiments, the device is customized to the user. Simulator 114 receives signals from modeling program 104 and produces electronic pulses based on models. The micro-electrodes stimulate relevant taste buds on the user's tongue to create the flavor sensation.

Client device 110 includes a user interface (UI) 116, which executes locally on client device 110 and operates to provide a UI to a user of client device 110. UI 116 further operates to receive user input from a user via the provided user interface, thereby enabling the user to interact with client device 110. In one embodiment, UI 116 provides a user interface that enables a user of client device 110 to interact with modeling program 104 of computing device 102 via network 120. In various examples, the user interacts with modeling program 104 in order to configure taste and heath models. In one embodiment, UI 116 is stored on client device 110. In other embodiments, UI 116 is stored on another computing device (e.g., computing device 102), provided that UI 116 can access and is accessible by at least modeling program 104 and taste profile 112.

Figure 2:
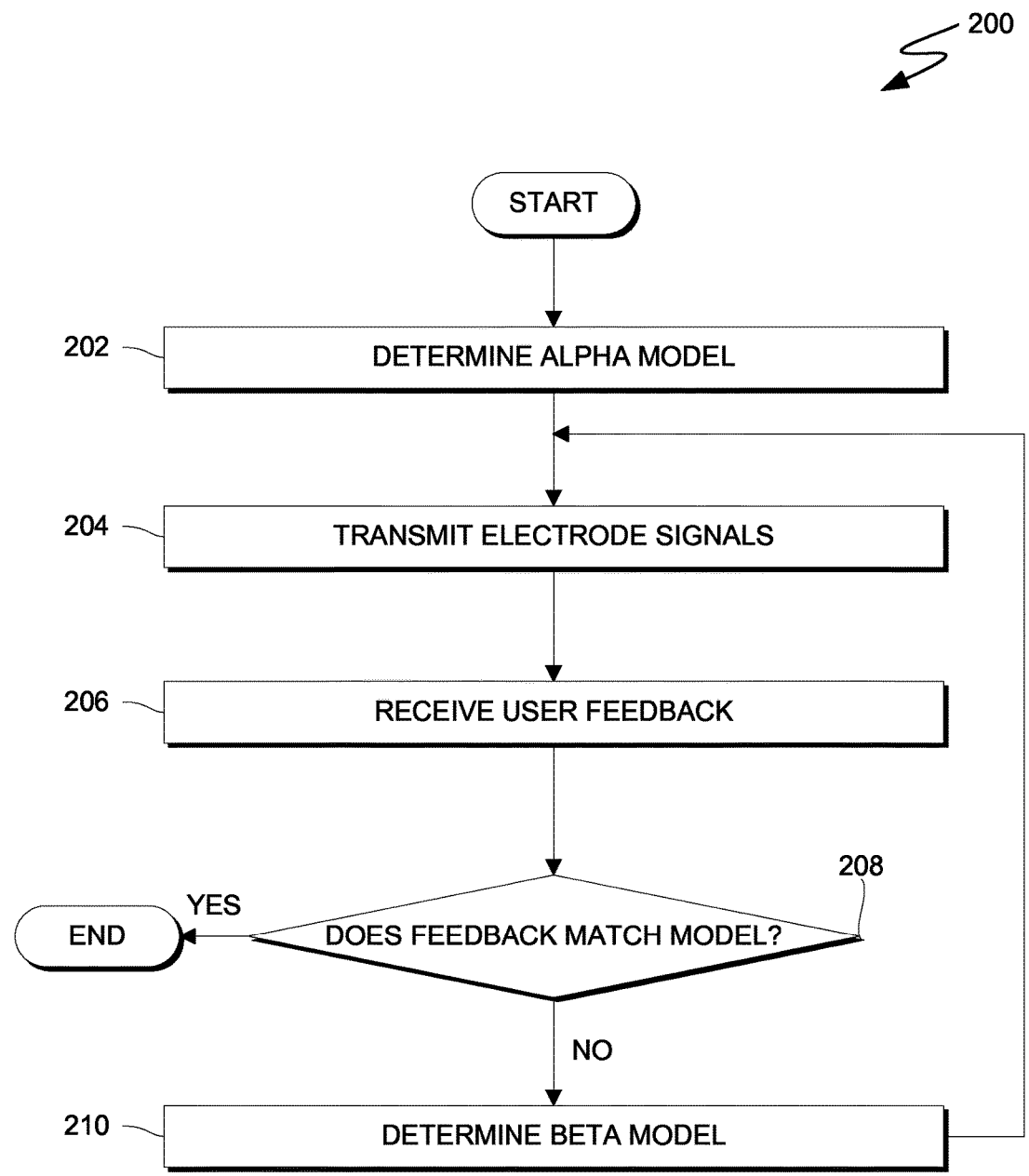
FIG. 2 is a flowchart depicting operations for modeling taste profiles, on a computing device within the computing environment of FIG. 1, in accordance with an embodiment of the present disclosure.

FIG. 2 is a flowchart depicting operations for modeling taste profiles, on a computing device within the computing environment of FIG. 1, in accordance with an embodiment of the present disclosure. For example, FIG. 2 is a flowchart depicting operations 200 of modeling program 104, on computing device 102 within computing environment 100.

In step 202, modeling program 104 determines an alpha model. In some embodiments, the alpha model is based on baseline values derived from other user data. For example, the average rating, based on all other users, for each taste vector is used. In other embodiments, an alpha model is created based on user responses to a questionnaire. For example, the questionnaire includes questions on regional preferences, user eating habits, favorite and least favorite foods, etc. In still other embodiments, the alpha model is based on data collected from laboratory testing. The alpha model is used as a standard, to which a user-specific model (i.e., beta model) can be derived. The alpha model includes taste vectors for each taste characteristic (e.g., salty, sweet, bitter, sour, and umami). The alpha model also includes various health vectors. In some embodiments, the user chooses which health vectors are included in the alpha model. In other embodiments, weight vectors are used to determine which health vectors have the most impact on the alpha model. The alpha model is stored in the database.

In step 204, modeling program 104 transmits electrode signals to the simulator. Modeling program 104 transmits electrode signals to the simulator that correspond to the model. In some embodiments, electrode signals correspond to the alpha model. In other embodiments, electrode signals correspond to the beta model. For example, the first time a user uses modeling program 104, alpha model electrode signals are sent to the simulator. Beta model electrode signals are sent to the simulator each subsequent time a user uses modeling program 104. Electrode signals stimulate a user's tongue by delivering electrical pulses to the user's taste buds. A combination of varying pulse strength and location of pulse on the user's tongue cause the user to experience different flavor profiles. In some embodiments, the varying pulse strength delivers flavor characteristics to a user (e.g., sweet, salt, bitter, sour, or umami). In this embodiment, the user is able to experience basic aspects of taste. In some embodiments, the varying pulse strength delivers a flavor profile matching a dish. In some embodiments, modeling program 104 instructs the simulator to release one or more chemicals from a chemical library within the simulator. The one or more chemicals replicate the scent of a dish, promoting the user's ability to virtually taste.

In step 206, modeling program 104 receives user feedback. The user interacts with a UI on the client device to provide feedback about the taste provided by the simulator in step 204. In some embodiments, the user provides quantitative feedback, such as a rating from one to five. In some embodiments, the user feedback is in the form of a like or a dislike. In other embodiments, the user provides qualitative feedback, such as a dish being to salty or not sweet enough. The user feedback is stored as the user taste profile. In some embodiments, the user taste profile is used to modify the alpha model of other dishes.

In some embodiments, the user feedback is used to determine a beta model. In these embodiments, the taste vectors and health vectors of the alpha model are modified to reflect a specific user's preference. In some embodiments, the user feedback is used to recommend restaurants and dishes to a user. For example, user feedback is used in a social media platform. In this example, a user's feedback is compared to user's with a similar taste profile to make recommendations.

In decision 208, modeling program 104 determines whether the user feedback matches the model. If modeling program 104 determines that the model matches the user feedback (decision 208, YES branch), then modeling program 104 finishes the model (END). In some embodiments, the user feedback has to match the model within a threshold variance. If modeling program 104 determines that the model does not match the user feedback (decision 208, NO branch), then modeling program 104 determines a beta model (step 210).

In step 210, modeling program 104 determines a beta model. Modeling program 104 uses the vectors from the alpha model and user feedback to determine a variance between the two values. A direction of the variance is also determined. For example, modeling program 104 determines whether a dish need more or less sweet. The variance is determined for each taste vector. For example, equation (2) is used to determine the beta model vectors.

$$\vec{T_\beta} = \vec{T_\alpha} + \alpha \Delta \vec{T_\alpha} \qquad (2)$$

In this equation, $T_\beta$ is the value for the beta model vector, $T_\alpha$ is the alpha model vector value, $\alpha$ is chosen based on iteration, and $\Delta T_\alpha$ is the variance between the alpha vector and user feedback. In some embodiments, the beta model is calculated whenever the absolute value of the variance is greater than a minimum accepted value. In other embodiments, the beta model is calculated for a set number of iterations. Modifications to the health vectors can be obtained from a chemical characterization of food (e.g., laboratory testing).

In some embodiments, the calculated beta vectors are used to make suggestions to a chef. For example, where a user prefers salty food, the calculated beta vector is used by the chef to modify a dish by adding more salt. In other embodiments, the calculated beta vectors are used by an application to provide a user with dining suggestions. For example, the application suggests a restaurant to dine at or a specific meal to order at a restaurant.

In some embodiments, operations 200 are paired with a virtual chef to provide virtual tasting recommendations to a user for novel dishes. For example, the virtual chef combines ingredients based on regional preferences and types of dishes to produce a dish. The virtual chef converts the dish into a model. The virtual chef model is put into terms of the taste and health vectors (e.g., alpha model). Electronic pulses are delivered to the simulator based on the model, to allow the user to sample the dish created by the virtual chef.

Figure 3:
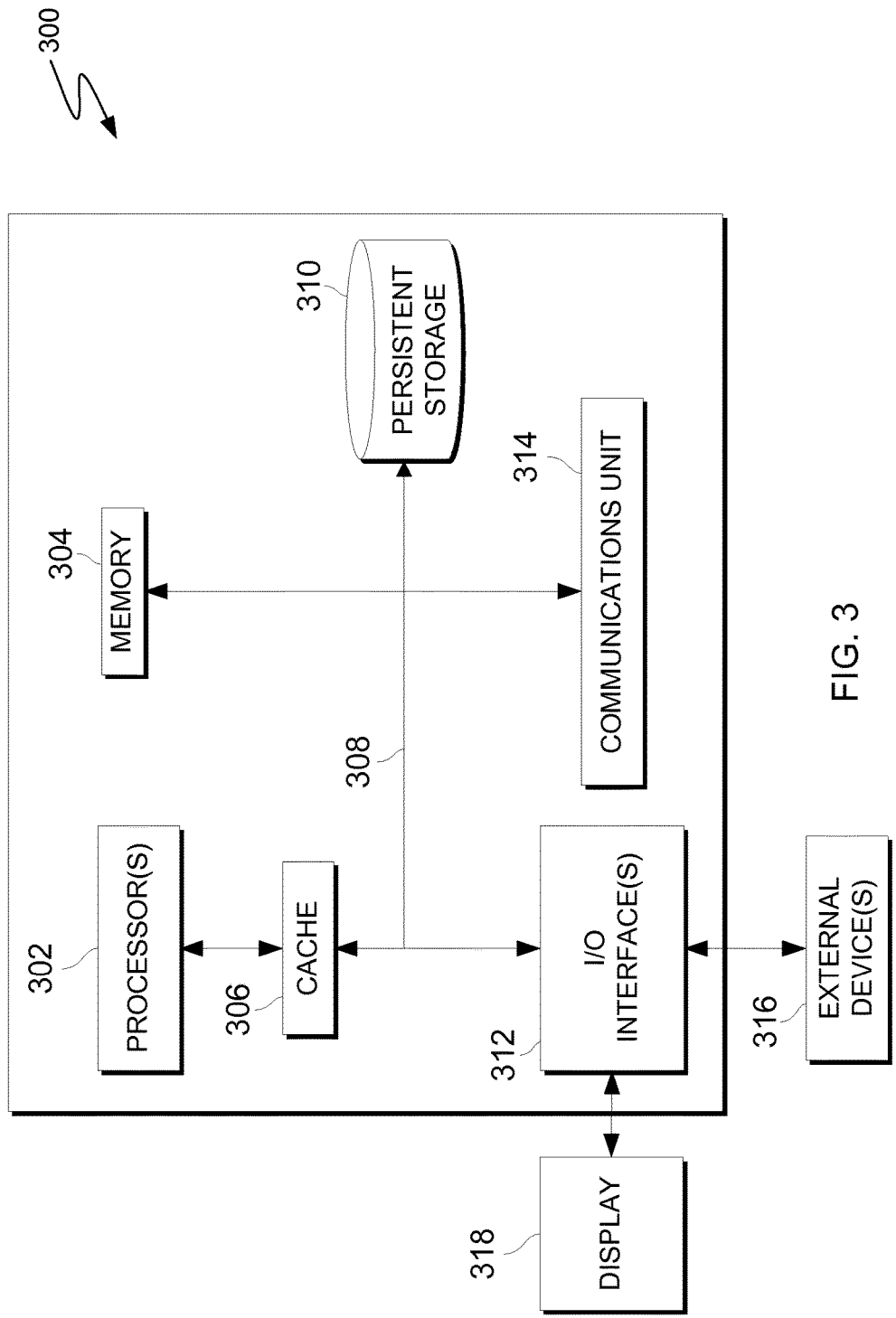
FIG. 3 is a block diagram of components of a computing device executing operations for modeling taste profiles, in accordance with an embodiment of the present disclosure.

FIG. 3 is a block diagram of components of a computing device, generally designated 300, in accordance with an embodiment of the present disclosure. In one embodiment, computing device 300 is representative of computing device 102. For example, FIG. 3 is a block diagram of computing device 102 within computing environment 100 executing operations of modeling program 104.

It should be appreciated that FIG. 3 provides only an illustration of one implementation and does not imply any limitations with regard to the environments in which different embodiments may be implemented. Many modifications to the depicted environment may be made.

Computing device 300 includes communications fabric 308, which provides communications between computer processor(s) 302, memory 304, cache 306, persistent storage 310, communications unit 314, and input/output (I/O) interface(s) 312. Communications fabric 308 can be implemented with any architecture designed for passing data and/or control information between processors (such as microprocessors, communications and network processors, etc.), system memory, peripheral devices, and any other hardware components within a system. For example, communications fabric 308 can be implemented with one or more buses.

Memory 304 and persistent storage 310 are computer-readable storage media. In this embodiment, memory 304 includes random access memory (RAM). In general, memory 304 can include any suitable volatile or non-volatile computer readable storage media. Cache 306 is a fast memory that enhances the performance of processors 302 by holding recently accessed data, and data near recently accessed data, from memory 304.

Program instructions and data used to practice embodiments of the present invention may be stored in persistent storage 310 and in memory 304 for execution by one or more of the respective processors 302 via cache 306. In an embodiment, persistent storage 310 includes a magnetic hard disk drive. Alternatively, or in addition to a magnetic hard disk drive, persistent storage 310 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 310 may also be removable. For example, a removable hard drive may be used for persistent storage 310. Other examples include optical and magnetic disks, thumb drives, and smart cards that are inserted into a drive for transfer onto another computer-readable storage medium that is also part of persistent storage 310.

Communications unit 314, in these examples, provides for communications with other data processing systems or devices, including resources of network 120. In these examples, communications unit 314 includes one or more network interface cards. Communications unit 314 may provide communications through the use of either or both physical and wireless communications links. Program instructions and data used to practice embodiments of the present invention may be downloaded to persistent storage 310 through communications unit 314.

I/O interface(s) 312 allows for input and output of data with other devices that may be connected to computing device 300. For example, I/O interface 312 may provide a connection to external devices 316 such as a keyboard, keypad, a touch screen, and/or some other suitable input device. External devices 316 can also include portable computer-readable storage media such as, for example, thumb drives, portable optical or magnetic disks, and memory cards. Software and data used to practice embodiments of the present invention (e.g., software and data) can be stored on such portable computer-readable storage media and can be loaded onto persistent storage 310 via I/O interface(s) 312. I/O interface(s) 312 also connect to a display 318.

Display 318 provides a mechanism to display data to a user and may be, for example, a computer monitor, or a television screen.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer program product, the computer program product comprising:

a computer readable storage medium and program instructions stored on the computer readable storage medium, the program instructions comprising:

program instructions to determine an alpha model for a user taste profile;

program instructions to transmit an electrode signal, corresponding to a taste profile, to a taste simulator, based on the alpha model;

program instructions to release at least one first chemical that replicates a scent of the taste profile, based on the alpha model;

program instructions to receive a user feedback on the taste profile introduced through the electrode signal and the at least one first chemical;

program instructions to determine a variance between the alpha model and the user feedback;

program instructions to compare the variance to a predetermined threshold;

in response to a determination that the variance is greater than the predetermined threshold, program instructions to generate a beta model for the user taste profile;

program instructions to transmit a second electrode signal to the taste simulator in combination with a release of at least one second chemical, wherein the second electrode signal and the at least one second chemical correspond to a taste profile of a food dish, based on the user taste profile; and program instructions to receive a second set of user feedback on the taste profile of the food dish introduced through the second electrode signal and the at least one second chemical.

2. The computer program product of claim 1, wherein at least one of the alpha model and the beta model are based, at least in part, on a taste vector, a health vector, and a weight vector.

3. The computer program product of claim 1, wherein the taste simulator delivers electric stimulation to a tongue of a user such that the taste profile is simulated for the user.

4. The computer program product of claim 2, wherein the taste vector comprises values for one or more of the tastes of sweet, salty, bitter, sour, and umami.

5. The computer program product of claim 2, wherein the health vector comprises values for one or more of calories, cholesterol, metabolic rate, and fat content.

6. The computer program product of claim 1, wherein the alpha model is based, at least in part, on a data from one or more users in a computing social network.

7. A computer system, the computer system comprising:
one or more computer processors;
one or more computer readable storage media;
program instructions stored on the computer readable storage media for execution by at least one of the one or more processors, the program instructions comprising:
program instructions to determine an alpha model for a user taste profile;
program instructions to transmit an electrode signal, corresponding to a taste profile, to a taste simulator, based on the alpha model;
program instructions to release at least one first chemical that replicates a scent of the taste profile, based on the alpha model;
program instructions to receive a user feedback on the taste profile introduced through the electrode signal and the at least one first chemical;
program instructions to determine a variance between the alpha model and the user feedback;
program instructions to compare the variance to a predetermined threshold;
in response to a determination that the variance is greater than the predetermined threshold, program instructions to generate a beta model for the user taste profile;
program instructions to transmit a second electrode signal to the taste simulator in combination with a release of at least one chemical, wherein the second electrode signal and the at least one second chemical correspond to a taste profile of a food dish, based on the user taste profile; and
program instructions to receive a second set of user feedback on the taste profile of the food dish introduced through the second electrode signal and the at least one second chemical.

8. The computer system of claim 7, wherein at least one of the alpha model and the beta model are based, at least in part, on a taste vector, a health vector, and a weight vector.

9. The computer system of claim 7, wherein the taste simulator delivers electric stimulation to a tongue of a user such that the taste profile is simulated for the user.

10. The computer system of claim 8, wherein the taste vector comprises values for one or more of the tastes of sweet, salty, bitter, sour, and umami, and wherein the health vector comprises values for one or more of calories, cholesterol, metabolic rate, and fat content.

11. The computer system of claim 7, wherein the alpha model is based, at least in part, on a data from one or more users in a computing social network.

12. The computer program product of claim 1, further comprising:
program instructions to generate a food recommendation, based on the beta model,
wherein the food recommendation is one or more of a restaurant recommendation, a chef recommendation, and a recipe recommendation.

13. The computer system of claim 7, further comprising:
program instructions to generate a food recommendation, based on the beta model, wherein the food recommendation is one or more of a restaurant recommendation, a chef recommendation, and a recipe recommendation.

* * * * *